United States Patent
Jhetam

(10) Patent No.: US 11,833,303 B2
(45) Date of Patent: Dec. 5, 2023

(54) WEARABLE CONCENTRATION IMPROVEMENT DEVICE

(71) Applicant: Imraan Feisal Jhetam, Exeter (GB)

(72) Inventor: Imraan Feisal Jhetam, Exeter (GB)

(*) Notice: Subject to any disclaimer, the term of this patent is extended or adjusted under 35 U.S.C. 154(b) by 250 days.

(21) Appl. No.: 17/166,485

(22) Filed: Feb. 3, 2021

(65) Prior Publication Data

US 2021/0236756 A1   Aug. 5, 2021

(30) Foreign Application Priority Data

Feb. 4, 2020 (GB) .................................... 2001480

(51) Int. Cl.
| | |
|---|---|
| *A61M 16/00* | (2006.01) |
| *A61M 16/06* | (2006.01) |
| *A61B 5/00* | (2006.01) |
| *A61B 5/145* | (2006.01) |
| *A61B 5/16* | (2006.01) |
| *A61B 5/11* | (2006.01) |

(52) U.S. Cl.
CPC ......... *A61M 16/024* (2017.08); *A61B 5/1114* (2013.01); *A61B 5/14542* (2013.01); *A61B 5/163* (2017.08); *A61B 5/6803* (2013.01); *A61B 5/7282* (2013.01); *A61M 16/0683* (2013.01); *A61B 2562/0219* (2013.01); *A61M 2202/0208* (2013.01); *A61M 2230/205* (2013.01); *A61M 2230/63* (2013.01)

(58) Field of Classification Search
CPC ............ A61M 16/024; A61M 16/0683; A61M 2202/0208; A61M 2230/205; A61M 2230/63; A61B 5/163; A61B 5/1114; A61B 5/14542; A61B 5/6803; A61B 5/7282
See application file for complete search history.

(56) References Cited

U.S. PATENT DOCUMENTS

| | | | |
|---|---|---|---|
| 4,559,941 A * | 12/1985 | Timmons .......... | A61M 16/0672 D16/322 |
| 5,928,189 A | 7/1999 | Phillips et al. | |
| 6,684,883 B1 * | 2/2004 | Burns ............... | A61M 16/0666 128/207.18 |
| 9,004,072 B2 * | 4/2015 | Barker .............. | A61M 16/0672 128/207.18 |
| 2002/0195105 A1 | 12/2002 | Blue et al. | |

(Continued)

FOREIGN PATENT DOCUMENTS

| | | |
|---|---|---|
| CN | 204389817 | 6/2015 |
| EP | 1082972 | 7/2000 |

(Continued)

OTHER PUBLICATIONS

PCT/IB2020/051747 Demand, Aug. 28, 2020.

(Continued)

*Primary Examiner* — Steven O Douglas
(74) *Attorney, Agent, or Firm* — William H. Bollman

(57) ABSTRACT

A wearable concentration improvement apparatus to identify trigger events has one or more sensor, a fluid channel for supply of gas from a unit to one or more gas outlets, and head securement to a user's head. The head securement positions the one or more outlets proximate the user's airway. The fluid channel provides gas to the one or more outlets according to identification of a trigger event by the apparatus.

18 Claims, 5 Drawing Sheets

(56) References Cited

U.S. PATENT DOCUMENTS

| | | | | |
|---|---|---|---|---|
| 2004/0050390 A1* | 3/2004 | Ishizuka | ............... | A61M 16/08 |
| | | | | 128/207.18 |
| 2006/0084877 A1* | 4/2006 | Ujhazy | ................ | A61B 5/0826 |
| | | | | 600/483 |
| 2014/0123980 A1* | 5/2014 | Rissacher | ............ | A61B 5/6803 |
| | | | | 128/204.23 |
| 2014/0261413 A1* | 9/2014 | Gibson | ............... | A61M 15/009 |
| | | | | 128/203.12 |

FOREIGN PATENT DOCUMENTS

| | | |
|---|---|---|
| GB | 2501368 | 10/2013 |
| WO | 2005/065540 | 7/2005 |

OTHER PUBLICATIONS

GB2001480.9, Combined Seach and Examination Report under Sections 17 and 18(3), dated Jul. 15, 2020.
GB2001480.9, Combined Seach and Examination Report under Sections 17 & 18(3), dated Jul. 15, 2020.
GB2001480.9, Seach Report under Section 17, dated Jul. 14, 2020.

* cited by examiner

WEARABLE CONCENTRATION IMPROVEMENT DEVICE

FIELD OF THE INVENTION

The present invention relates to wearable concentration improvement device, in particular a device for improving a person's ability to concentrate and stay alert.

BACKGROUND

Increasing workloads and stress levels are common in many societies. Added to this many people in many societies are suffering from a lack of sleep.

In addition or the alternative the pressures of coping are exacerbated by a lack of sleep leading to general fatigue in many moments of life. It can be difficult to concentrate when tired.

Keeping blood oxygen at a healthy level is important. When levels are adequate, the body is able to deliver oxygen to the brain, heart and muscles and help them to function properly. When they are low, blood does not contain as much oxygen and the subject is likely to feel tired.

PRIOR ART

The present invention arose in order to overcome problems suffered by existing devices.

SUMMARY OF THE INVENTION

According to a first aspect of the present invention there is provided wearable concentration improvement device comprising: a fatigue event identification apparatus arranged to identify a trigger event indicating fatigue of a user; a fluid channel is arranged to supply gas from a gas supply unit to one or more gas outlets which are proximate the user's face; and a head securement means which is worn on the user's head, wherein the fatigue event identification apparatus is operative to transmit a signal indicating the trigger event to the gas supply unit, and the gas supply unit is arranged to provide gas to the one or more gas outlets which are retained in position by the head securement means.

According to another aspect of the invention there is a wearable concentration improvement device comprising: an apparatus for identifying trigger events comprising one or more sensor; a fluid channel for supply of gas from a unit to one or more gas outlets; and a head securement means for a user's head; wherein the head securement means is adapted to position the one or more outlets proximate the user's airway, and the fluid channel is arranged to provide gas to the one or more outlets according to identification of a trigger event by the apparatus.

It may be envisaged that one, two or more of the gas outlets in use may be located proximate the user's nostrils.

The wearable concentration improvement device may be wearable as a sole piece on the user's head. The head securement may support or comprise other components of the wearable concentration device. For example the other components may include the fatigue event identification apparatus, the sensor(s), the gas supply unit(s), the fluid channel(s), and the gas outlet(s).

The head securement means may comprise a hat. So for example a person may be standing as a guard or sentry many hours in hot sun or on a dark night with the wearable concentration device secured on their head by the hat. So the guard may be able to stay highly alert and prevent an art heist by a thief or a sneak attack by an assassin because of the alert stimulus provided by the wearable concentration device.

The head securement means may comprise headphones having a head strap connecting two ear coverings. So for example a person may be on standby at an overnight taxi service using the headphones to monitor for incoming calls from drivers and customers. The person may be able to stay highly alert and take a call from a customer stranded a remote location requiring an urgent taxi to shelter because of the alert stimulus provided by the wearable concentration device.

The head securement may comprise spectacles or reading glasses having a frame including arms that rest over the wearer's ears and a nose bridge. So for example a person monitoring screens which display status of a state network electrical grid and may be able to stay highly alert to prevent an electricity blackout.

The head securement may comprise the fatigue event identification apparatus.

The trigger event apparatus may be arranged to identify and respond to trigger events detected by the trigger event sensors to supply of gas to the one or more outlets. The trigger event apparatus may involve control of supply to the gas to the outlet or outlets, control of quantity and/or control of quality. The fatigue event identification apparatus may be arranged to adjust a flow and/or concentration of air, and/or oxygen, and/or oxygen enhanced air, and/or other gases in air such as nitrogen and/or carbon dioxide. to the one or more gas outlets according to data gathered from the trigger event sensor(s).

In this way the device may be arranged to provide supplemental oxygen to a user who is apparently suffering fatigue, upon identification of symptoms of fatigue by the apparatus. This supplemental oxygen advantageously therefore provides greater awareness and an accompanying concentration improvement.

The trigger events may be provided by the trigger event sensors which detect external or local factors which the fatigue event identification apparatus is either predisposed to identify and recognize or adapted to learn to do so. The wearable concentration improvement device may comprise a fatigue event identification apparatus arranged to identify trigger events indicating fatigue of a user. Then the fatigue event identification apparatus may receive signals from the sensor(s) and then identify the events as trigger events because the events indicate the user is fatigued and has low alertness and concentration ability.

For example trigger events may comprise timing related events. For example in some embodiments the fatigue event identification apparatus may comprise a timer for controlled activation of the gas outlets or identification of trigger events and decision making to control the gas supply unit(s), fluid channel(s), and/or gas supply outlet(s) based on trigger event patterning, sequencing and/or timing.

The securement means may provide, support of have disposed in or on it, one or more of the trigger event sensors.

The wearable concentration improvement device may comprise a trigger event sensor for detecting atmospheric conditions which the fatigue event identification apparatus may identify as atmospheric trigger events which affect a person's ability to concentrate or stay alert. The atmospheric sensor may be arranged to measure atmospheric temperature or humidity or altitude or oxygen level in the ambient air or level a gas which can reduce alertness such as carbon monoxide. The atmospheric sensor may be arranged to detect light or darkness because people tend to be more alert in bright light and sleepy in the dark.

Other trigger event sensors may be sensitive to physical characteristics or biological characteristics of the person user.

The wearable concentration improvement device may comprise a trigger event sensor which is an oximeter arranged to measure the wearers internal oxygen level in their blood. The oximeter may be arranged to communicate with the fatigue event identification apparatus. The trigger event apparatus may be arranged to identify a low blood oxygen level detected by the oximeter as one of the trigger events. The oximeter may be a pulse type of oximeter. It pulses light into the wearer through their skin and measures oxygen level in the blood from the light reflected or transmitted.

The wearable concentration improvement device may be arranged to hold the oximeter on the user or so that it is directed at the user in use. For example the oximeter may be located in contact with the user's nose or ears or similar. This oximeter may be arranged to identify the user's blood oxygen saturation level (SpO2).

The wearable concentration improvement device may comprise a pupil sensor for monitoring pupil size which senses instability of pupil size and/or constriction of a pupil (miosis). The fatigue event identification apparatus may include the pupil sensor.

Nodding head movements of a person's head and drooping head movements are indicative of fatigue. Drooping head movements may be determined by their pattern, timing or severity to be trigger events indicative of fatigue.

The wearable concentration improvement device may comprise an orientation sensor, for example a gyroscope or an accelerometer. The orientation sensor may be able to detect when the position changes. It may be able to detect actual acceleration of the sensor itself. It may be able to detect a gravitational acceleration and thereby a position relative to vertical may be deduced from the sensor signal.

The orientation sensor(s) communicate with the fatigue event identification apparatus to identify the head drooping movements which tilt laterally and also forward or backward and when the head twists.

The fatigue event identification apparatus may include a head orientation sensor which senses head movements indicative of fatigue.

In use the head securement is worn on the user's head. So the head securement may comprise a head orientation sensor to communicate nodding or drooping head movements or a drooped down head position to the fatigue event identification apparatus. The orientation sensor may be disposed on or inside the head securement. The orientation sensor may comprise a plurality of devices for detecting orientation. The alertness and concentration improving gas is then provided through the fluid channel to the one or more gas outlets according to identification of the trigger events by the event indication apparatus.

The plurality of orientation sensors may be disposed on opposite lateral sides of the head securement or on at least one lateral side. Ear covers or ear rests of the head securement are ideal for supporting the orientation sensors. A person wearing the head securement may suddenly tilt their head sideways or twist their neck as they nod off to sleep. The orientation sensors located on lateral sides are positioned where there is a relatively great amount of change in speed and so their sensitivity to these movements is good.

The plurality of orientation sensors may be disposed on front and/or rear sides of the head securement. Nose bridged rests, forehead rests and straps, and rear head straps and rests of the head securement are ideal for supporting the orientation sensors. A person wearing the head securement may suddenly tilt their head forward or backward as they nod off to sleep. The orientation sensors located on front and rear sides are positioned where there is a relatively great amount of change in speed and so their sensitivity to these movements is good.

The orientation sensor(s) may be located in a head securement hat rim or hat brim or at the top of the hat where nodding motions are accentuated by their distance from the person's neck axis of rotation. The orientation sensor(s) may be located in a head securement headphones ear covers, in the head strap connecting the ear covers and/or at the end of a microphone boom extend from an ear cover to in front of the wearer's mouth. The orientation sensor(s) may be held in head securement spectacles.

The spectacles may have lateral arms that rest on the sides of the wearer's head. The lateral arms may support an orientation sensor on a lateral side of the user's head in use. Each lateral arm may have an orientation sensor. So a right one of the lateral arms supports a right lateral orientation sensor and a left one of the lateral arms may support a left lateral orientation sensor. The spectacles may have a forehead bridge between the arms and a nose bridge to hold the glass lenses and rest on the wearer's nose. An orientation sensor may be disposed in or on the forehead bridge and/or the nose bridge. This orientation sensor may be most sensitive to the head tilting forward or backward or turning with a neck twist. The orientation sensor on the bridge may be used in combination with other orientation sensors in the lateral arms to detect the head drooping movements tilting forward/backward and laterally and turning.

The spectacles or hat may comprise an eye pupil sensor and/or an eye blinking sensor which senses a rate of blinking of a user's eye and transmit this information to trigger event identification sensor. The pupil sensor or eye blinking sensor may be disposed on the nose bridge or portion of the spectacles which holds the lenses or in the hat rim or brim.

The wearable concentration improvement device may comprise a fluid channel arranged to supply an alertness and concentration improving gas from a gas supply unit to gas supply outlets held near a wearer's airway e.g. mouth or nostrils.

The fluid channel may comprise a flexible tube. A portion of the flexible tube may be disposed along the arms of the spectacles. The flexible tube may be connected to a gas capsule disposed on the spectacle arms. The flexible tube may be disposed to bring gas from behind wearer's head to a gas outlet on the nose bridge of the spectacles. There may be gas outlets located on the cheek portion of the spectacles frame 5 below the lenses so as to direct towards and below the nasal bridge's nose pads. In use the gas flows out of the outlets by the wearer's nostrils and upper lip. Behind the wearer's head the flexible tube may be arranged as a head-strap connected to right and left lateral arms of the spectacles.

The gas supply unit may be a portable piece separate from a wearable portion of the wearable concentration improvement device comprising the head securement which the user wears on their head. The gas supply unit may be connected to the wearable portion by the fluid channel. The gas supply unit may be a relatively large unit too large and bulky to be part of the wearable portion of the wearable concentration improvement device.

In some embodiments the gas supply unit comprises a displaceable or removable reservoir of fluid or compressed gas. The fluid channel may comprise tubing from the displaceable reservoir.

The gas supply unit may be a pencil size capsule charged with the alertness and concentration improving gas. The capsule may be part of the wearable concentration improvement device which is worn in use by a person. The gas supply unit may be arranged to supply to one or more gas outlets on the wearable concentration improvement device.

The wearable concentration improvement device may comprise a second gas supply unit or second capsule charged with a second gas. The improvement device may comprise an ambient air inlet. The second gas supply unit or second capsule or ambient air inlet may also be connected to the fluid channel so that a mixture flow rate or concentration of a gas from the first or second gas supply unit or capsule may be regulated according to the trigger events.

The wearable concentration improvement device comprises an oxygen enricher. The oxygen enricher may comprise a compound which selectively absorbs a type of gas in air other than oxygen. The oxygen enricher may be a filter or a membrane which selectively blocks a type of gas air other than oxygen. The type of gas absorbed or blocked may be carbon dioxide. The compound may be a zeolite. The oxygen enricher may be comprised in a separate and/or separable gas supply unit that is separate from the head securement. The oxygen enricher may be disposed on or in the head securement. In this the wearable concentration improvement device may be wearable as sole piece on the user's head.

The wearable concentration improvement device may keep the wearer's blood oxygen level above a limit or between limits for good alertness and concentration ability by providing the gas according identification of a trigger event by the fatigue event identification apparatus.

The gas supply unit is envisaged may be battery-powered and may be combined with further functionality for or within the wearable concentration improvement device. For example the gas supply unit may be controlled and activated to dispense gas by the fatigue event identification apparatus.

The gas supply unit may be disposed on or in the head securement. The head securement may be adapted to position the one or more gas outlets proximate the user's airway entry.

The wearable concentration improvement device may comprise an ionizer to enhance the air quality. The ionizer may be fluidically connected to the fluid channel and operable the fatigue event identification apparatus. Ionized gas may be provided to the gas outlets according to identification of a trigger event or selected trigger events or pattern thereof.

In some embodiments the wearable concentration improvement device comprises a control means, for example comprising a display means. Such display means may be envisaged to display information relating to the sensed trigger events. Such control means may be envisaged to control the apparatus or one or more outlets.

In some embodiments the control and display means are comprised in the unit, combined with the oxygen enricher. In some embodiments the display and/or control means may be comprised in an independently available or separate item, for example a smartphone or personal computer. The wearable concentration improvement device may be envisaged to comprise a transceiver in such embodiments for example so as to wireless connect through intermachine operability such as Bluetooth®, radio waves or similar. In some embodiments the unit comprises a belt clip, such that a user is enabled to keep the unit with them at all times.

The invention will now be described, by way of example only, with reference to the accompanying figures in which:

DETAILED DESCRIPTION OF THE INVENTION

Figure 1:
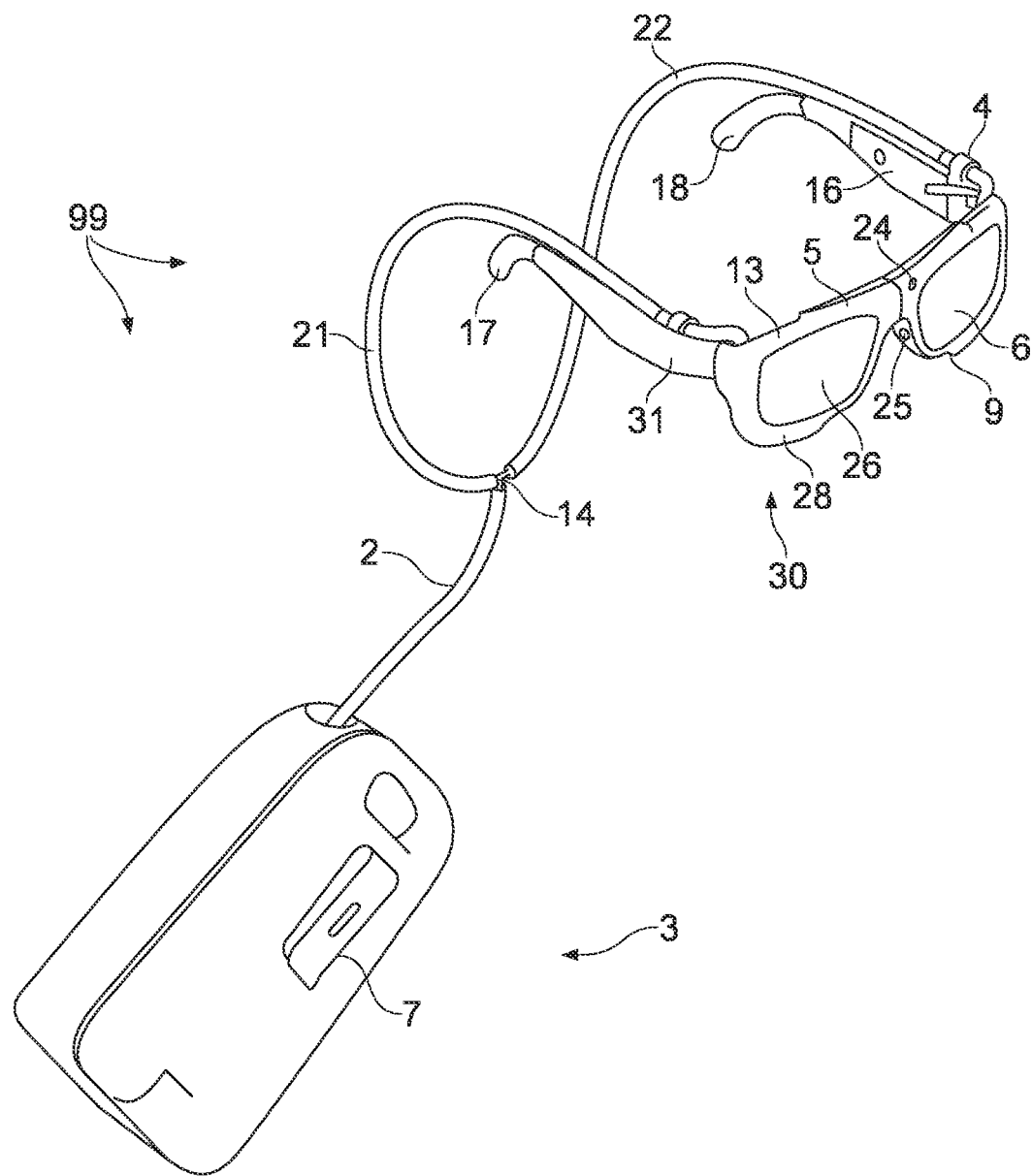
FIG. 1 shows an isometric view of wearable concentration improvement device.
Figure 5:
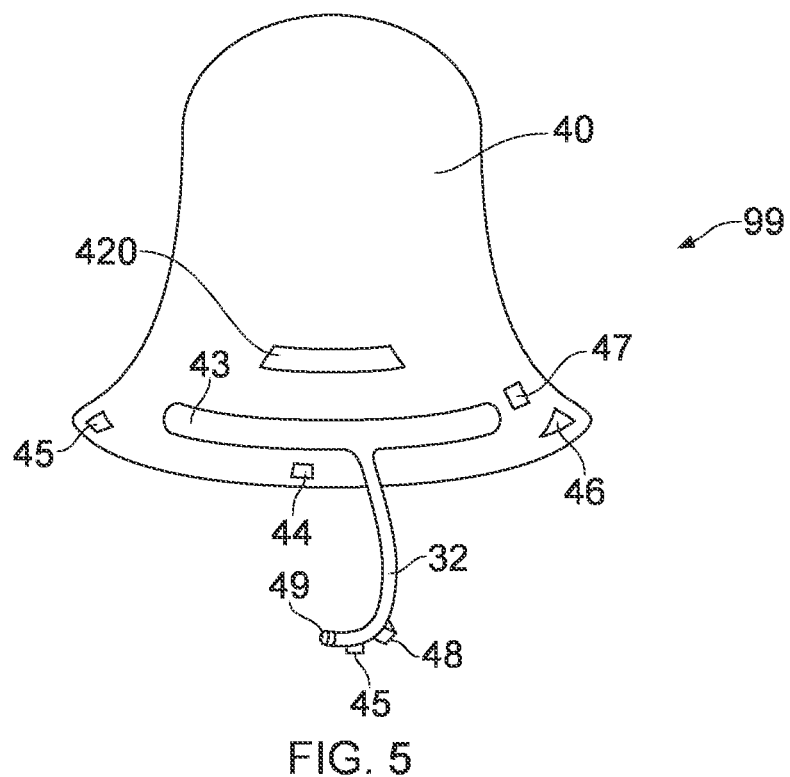
FIG. 5 shows a view of a wearable concentration improvement device in which the head securement comprises a hat.
Figure 6:
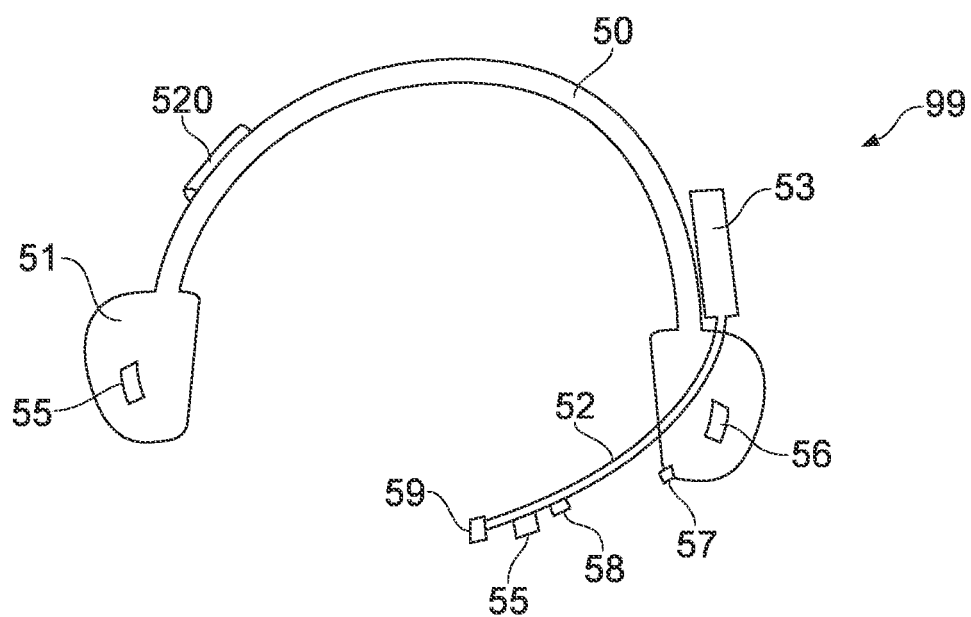
FIG. 6 shows a view of a wearable concentration improvement device in which the head securement comprises headphones.

With reference to the figures there are shown in FIG. 1, FIG. 5 and FIG. 6 examples the wearable concentration improvement device 99 in which the head securement comprises spectacles 30, and a hat 40 and headphones 50 respectively.

Figure 2:
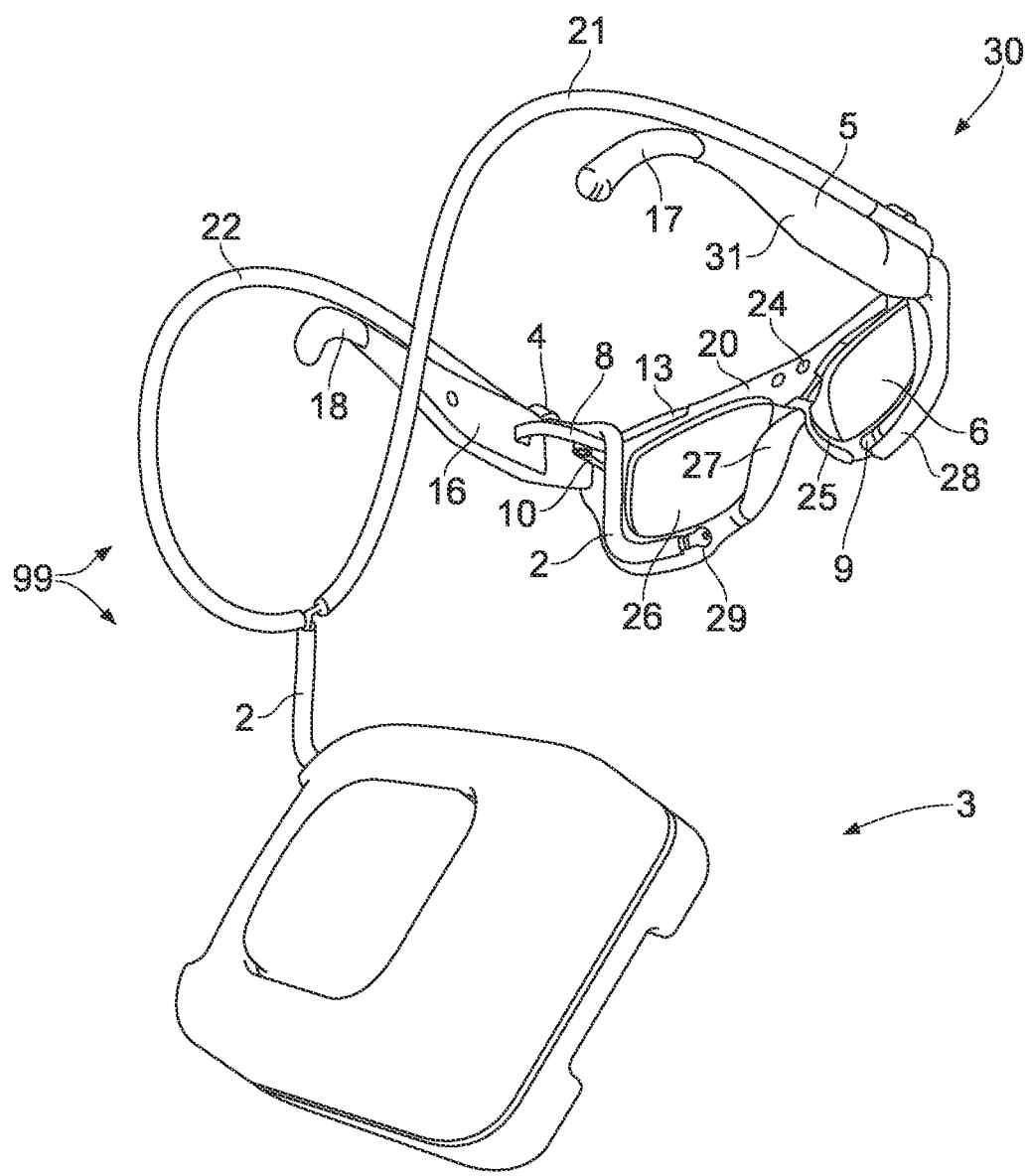
FIG. 2 shows a reverse isometric view of the wearable concentration improvement device shown in FIG. 1.
Figure 3:
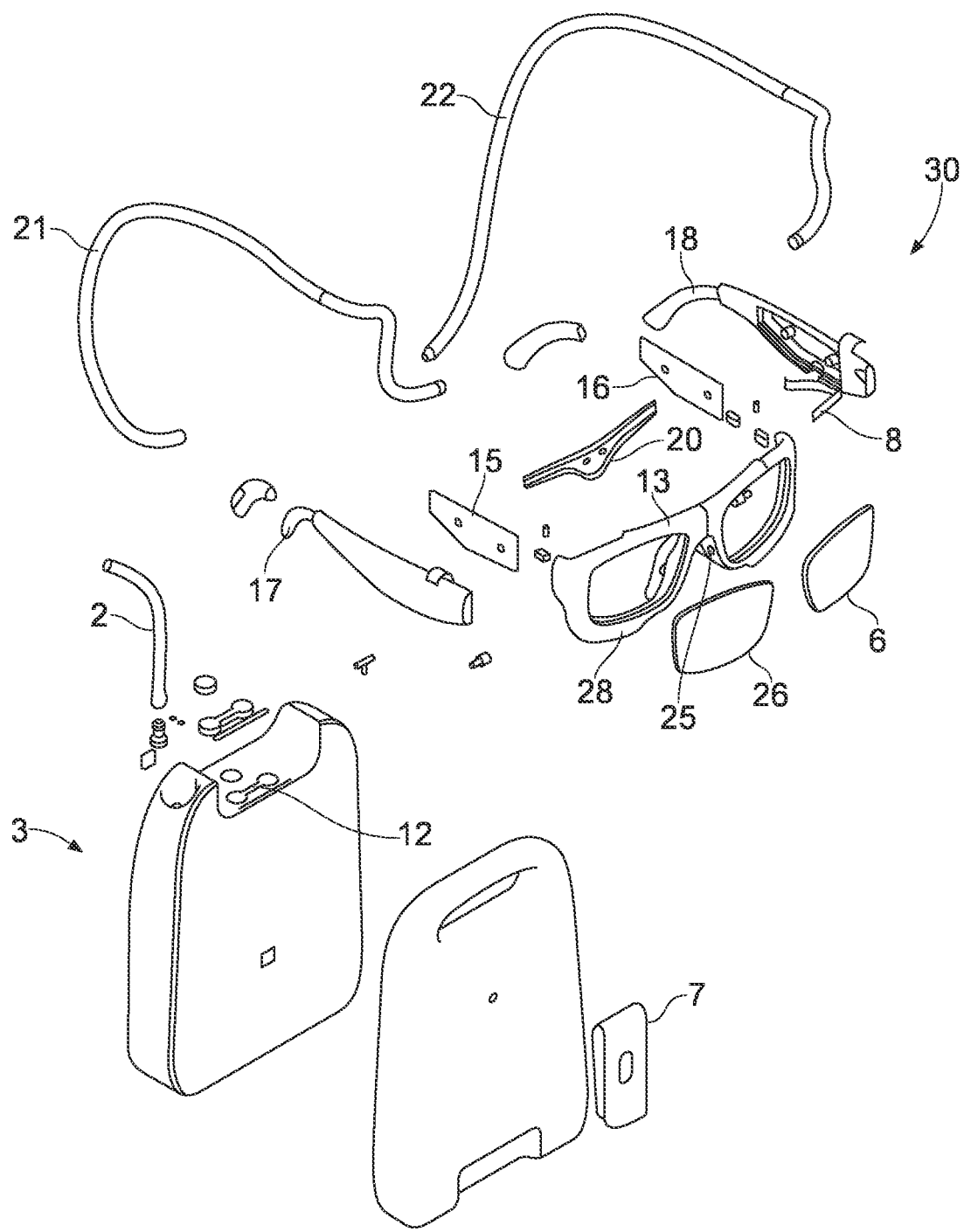
FIG. 3 shows an isometric exploded view of the wearable concentration improvement device shown in FIG. 1.
Figure 4:
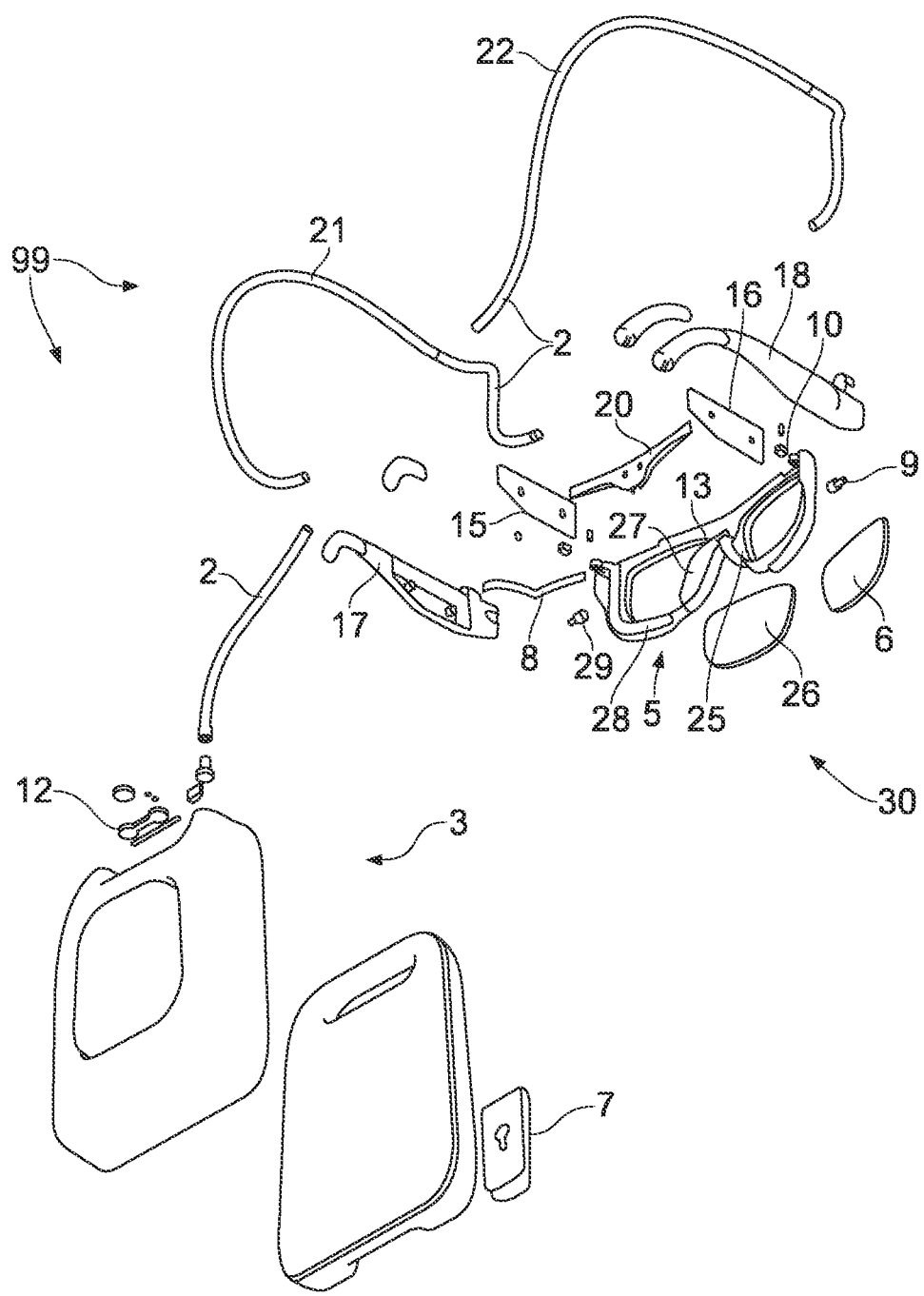
FIG. 4 shows a reverse exploded isometric view of the wearable concentration improvement device shown in FIG. 1.

As shown in detail in FIG. 1 and FIG. 2, the wearable concentration improvement device 99 comprises a fatigue event identification apparatus 20 for identifying trigger events comprising one or more trigger event sensors 15, 16, 24, 25, a fluid channel 2 for supply of gas from a gas supply unit 3 to two gas outlets 9, and a head securement means 30 for a user's head, wherein the head securement means is adapted to position the one or more outlets proximate the user's airway, and the fluid channel 2 is arranged to provide gas to the outlets 9 according to identification of a trigger event by the fatigue event identification apparatus 20.

The wearable concentration improvement device (99) is able to improve concentration, alertness and wakefulness of a person wearing it. The wearable device 99 comprises an event identification apparatus 20 arranged to take in signals from trigger event sensors 15, 16, 24, 25 which measure biological conditions of the wearer. The trigger event sensors include orientation sensors 15, 16, 24 to detect the orientation of the head of the person wearing the wearable device 99. The trigger event sensors include an oximeter 25 to detect oxygen level in the blood of person. The biological conditions that these trigger event sensors detect or measure indicate fatigue in the person which reduces their ability to concentrate.

When the person is tired, the oxygen level in their blood can be lower than when they are fully alert. When they are tired, their head may nod and droop. These trigger events trigger the wearable concentration improvement device 99 to provide a gas through the fluid channel 2, 21, 22 to the gas outlets 9 by the wearer's mouth and nose. As the wearer's alertness and concentration improves, the oxygen level in their blood rises and their head stops nodding and drooping. These new trigger events trigger the fatigue event identification apparatus 20 to activate the gas supply unit 3, fluid channel 2, 21, 22 and/or gas outlets 9 of the wearable concentration improvement device 99 to stop or alter the gas provided through the gas outlets 9 depending on the new trigger events. In this way the person wearing the wearable concentration improvement device 99 is kept alert. In particular reference to the example of the wearable concentration improvement device 99 shown in the FIGS. 1, 2, 3 and 4, a pair of spectacles is the head securement means 30. The spectacles 30 comprise see through lenses 6 and a frame 5. The lenses 6 may be tinted and/or prescription.

As shown in the example of FIGS. 1 to 4, the wearable concentration improvement device further comprises a connected gas supply unit 3 which is separate from the head securement 30. As shown in other examples in FIGS. 5 and 6, the wearable concentration improvement device further comprises a gas supply unit (43, 53) which is attached to the head securement so that whole the wearable concentration improvement device 99 may be worn as a sole piece on the head.

The gas supply unit 3 has a reservoir for one or more gases and/or an oxygen enricher. The gas supply unit reservoir(s) and/or concentrator is fluidically connected to the spectacles (30) by the fluid channels 2, 21, 22. The gas supply unit 3 comprises a small portable oxygen enricher and provides both power for the device and an ionized oxygen flow, as well as a belt clip 7 and simple local control means 12.

The spectacles 30 have arms 17, 18. The spectacles have a frame 5 to which the arm 17, 18 are sprung at hinge springs 10. There are clips 4 on the arms 17, 18 to attach the fluid channels 21, 22 to the arms 17, 18, which fluid channels may also in part be enclosed within the frame. The fluid channel 21, 22 is formed by tubing on either arm 17, 18 of the frame 5. Said tubing is formed of flexible or inflexible or inelastic or elastic material which may be resilient. Examples of such material polyethylene or silicone tubing however other materials suitable for transferring the gas may also be used. The tubing connects at a T junction 14 behind the head in use, and a single tube 2 leads to the unit.

The outlets 9 comprise small valves located in use to outlet between the lenses low proximate a nasal bridge 27, so as to be directed below the lenses 6 and frame 5 and into an area proximate in use to a user's nostrils. The gas outlet 9, 29 valves are in communication with the fatigue event identification apparatus 20. So the valves may be activated and operated according to any trigger event identified.

The tubing 2, 21, 22 of the fluid channel 2 is clipped over the arm hinges 10 and down the outer sides of the lenses 6 and below them. The tubing 21, 22 gas outlets 9, 29 are located on the cheek portion 28 of the spectacles frame 5 below the lenses 6 so as to direct towards and below the nasal bridge's 27 nose pads. The fluid channel 2 or a portion of it may be internal to the spectacles frame 5 which may have an internal conduit in the arms 17, 18 and in the cheek portion 28 of the frame 5 below the lenses 6.

The forehead bridge 13 of the frame 5 comprises the fatigue event identification apparatus 20 having sensors, namely a paranasal pulse oximeter 25. This sensor 25 is arranged to communicate data in reference to the blood oxygen saturation levels of the blood of the wearer and provide to data to the fatigue event identification apparatus to control the gas outlets 9 valves.

The spectacles' arms 17, 18 comprise a controller 11, with micro-USB (universal serial bus) connector and a transceiver for communication with the gas supply unit 3 and/or the fatigue event identification apparatus 20. The arms 17, 18 and forehead bridge 13 of the spectacles frame 5 are connected via ribbon electrical connectors 8.

The spectacles' arms 17, 18 further comprises head orientation sensors. There is a head orientation sensor 15 in the right arm 17, a head orientation sensor 16 in the left arm 18, and a head orientation sensor 24 in the nose bridge 27 or forehead bridge portion 13 of the frame 5 intermediate the spectacles' arms 17, 18. The head orientation sensors 15, 16, 24 comprise a three-axis accelerometer and/or a gyroscope. These are arranged to communicate data in reference to the head movements of the user, wherein drooping head movements for example may be envisaged and programmed into the fatigue event identification apparatus 20 to to indicate or identify a trigger event that is likely fatigue.

An atmospheric sensor 31 is a trigger event sensor included on the spectacle arm 17 midway between the forehead bridge 13 and ear rest. It could also be on other part of the frame 5 where it is located away from user's skin so as not to be directly affect by the user's body and breath.

The fatigue event identification apparatus processes the data gathered from the, atmospheric sensor, pulse oximeter and the accelerometer and operates the gas supply unit 3, fluid channels 2, 21, 22, and/or gas outlet 9 valves to adjust the oxygen flow accordingly.

By increasing the SpO2 level the users will feel more alert and focused. The level of concentration is displayed on the oxygen enricher. The user can also manually adjust this.

A linked smartphone application will track the user's usage and the changes in SpO2.

FIG. 5 shows a wearable concentration improvement device 99 in which the head securement comprises a hat 40; and FIG. 6 shows one in which the head securement 50 comprises a headphone.

As shown in FIGS. 5 and 6 the head securement may itself support the fatigue event identification apparatus 20, the gas supply unit 3, the fluid channel 2, and the gas outlet(s) 9 whereby the wearable concentration improvement device is wearable as a sole piece on the user's head.

FIG. 5 shows the gas supply unit 43 is a capsule attached to the exterior of the hat 40. The capsule is pencil shaped and parallel to the brim. The fluid channel 32 is connected to the gas supply unit 43. The fluid channel goes over the brim down to the gas outlet 49. There is an oximeter 45 by the gas outlet. There is also a head orientation sensor 48 on the fluid channel 32 by the gas outlet 49. On the brim there are head orientation sensors 44, 45, 46 and also another oximeter 47 which is arranged to be pressed on the wearer's temple. The fatigue event identification apparatus 420 is attached to the hat 40 above the gas supply unite 43.

FIG. 6 shows the gas supply unit 53 is block or disk-shaped capsule attached to the head strap which connects the earphones 51 of the headphones 50. The fluid channel 52 is connected to the gas supply unit 53. The fluid channel 52 extends from an earphone out to the gas outlet 59 where there is gas valve and a microphone. There is an oximeter 55 by the gas outlet. There is also a head orientation sensor 58 on the fluid channel 52 by the gas outlet 59. On the earphones there are head orientation sensors 56, 56 and also another oximeter 57 which is arranged to be pressed on the wearer's earlobe. The fatigue event identification apparatus 520 is attached to the head strap above the left earphone 55.

The invention has been described by way of examples only and it will be appreciated that variation may be made to the above-mentioned embodiments without departing from the scope of invention as defined by the claims, in particular but not solely combination of features of described embodiments.

The invention claimed is:

1. A wearable concentration improvement device comprising:

a fatigue event identification apparatus arranged to identify a trigger event indicating fatigue of a user;
a fluid channel arranged to supply gas from a gas supply unit to one or more gas outlets which are proximate the user's face; and
a head securement means which is worn on the user's head, wherein the fatigue event identification apparatus is operative to transmit a signal indicating the trigger event to the gas supply unit,
the gas supply unit is arranged to provide gas to the one or more gas outlets which are retained in position by the head securement means, and
the fatigue event identification apparatus includes a head orientation sensor which senses head movements indicative of fatigue.

2. The wearable concentration improvement device according to claim 1 wherein the fatigue event identification apparatus includes an oximeter to sense a blood oxygen level indicative of fatigue.

3. A wearable concentration improvement device comprising:
a fatigue event identification apparatus arranged to identify a trigger event indicating fatigue of a user;
a fluid channel arranged to supply gas from a gas supply unit to one or more gas outlets which are proximate the user's face; and
a head securement means which is worn on the user's head, wherein
the fatigue event identification apparatus is operative to transmit a signal indicating the trigger event to the gas supply unit,
the gas supply unit is arranged to provide gas to the one or more gas outlets which are retained in position by the head securement means, and
the fatigue event identification apparatus includes a pupil sensor for monitoring pupil size which senses instability of pupil size and/or constriction of a pupil.

4. A wearable concentration improvement device comprising:
a fatigue event identification apparatus arranged to identify a trigger event indicating fatigue of a user;
a fluid channel arranged to supply gas from a gas supply unit to one or more gas outlets which are proximate the user's face; and
a head securement means which is worn on the user's head, wherein
the fatigue event identification apparatus is operative to transmit a signal indicating the trigger event to the gas supply unit,
the gas supply unit is arranged to provide gas to the one or more gas outlets which are retained in position by the head securement means, and
the fatigue event identification apparatus includes an eye blinking which senses a rate of blinking of a user's eye.

5. The wearable concentration improvement device according to claim 1 wherein the one or more gas outlets are supported in use by the head securement proximate the user's airway entry.

6. The wearable concentration improvement device according to claim 1 wherein the fatigue event identification apparatus is operative to adjust flow rate or concentration of oxygen in the gas provided to the gas outlet(s) according to a specific trigger event.

7. The wearable concentration improvement device according to claim 1 wherein the head orientation sensor comprises an accelerometer.

8. The wearable concentration improvement device according to claim 1 wherein the head securement means supports the fatigue event identification apparatus.

9. The wearable concentration improvement device according to claim 1 wherein the fluid channel comprises a flexible tube arranged as a head-strap portion of the head securement.

10. The wearable concentration improvement device according to claim 1 wherein the head securement means includes a hat having a brim comprising the head orientation sensor.

11. The wearable concentration improvement device according to claim 1 wherein the head securement means includes headphones having an earphone comprising the head orientation sensor.

12. The wearable concentration improvement device according to claim 1 wherein the head securement means includes a pair of spectacles.

13. The wearable concentration improvement device according to claim 12, wherein the fluid channel comprises a flexible tube arranged as a head-strap connected to right and left lateral arms of the spectacles.

14. The wearable concentration improvement device according to claim 12 wherein a right and left lateral arms of the spectacles support a right and a left head orientation sensor respectively to communicate with the fatigue event identification apparatus to identify laterally tilting head drooping movements.

15. The wearable concentration improvement device according to claim 12 wherein spectacles have a bridge which supports a front head orientation sensor on a front of the user's head in use.

16. The wearable concentration improvement device according to claim 15 wherein the spectacles further comprise a lateral arm which supports a lateral head orientation sensor to detect head drooping movements tilting forward/backward and laterally.

17. The wearable concentration improvement device according to claim 12, wherein the gas outlets are located in or on a cheek portion of a frame below lenses of the spectacles so as to direct towards and below a nasal bridge's nose pads.

18. The wearable concentration improvement device according to claim 1 wherein the head securement means comprises a frame which supports the fatigue event identification apparatus, the gas supply unit, the fluid channel, and the gas outlet(s) whereby the wearable concentration improvement device is wearable as a sole piece on the user's head.

* * * * *